US008337894B2

(12) United States Patent
Goetz et al.

(10) Patent No.: US 8,337,894 B2
(45) Date of Patent: Dec. 25, 2012

(54) PROCESS OF MANUFACTURING A SOLID COSMETIC PRODUCT

(75) Inventors: Nadine Goetz, Villeneuve le Roi (FR); Blandine Hingant, Bois Colombes (FR); Christian Salciarini, Couilly (FR); Jean-Luc Lambrecq, Choisy au Bac (FR); Michel Siodmak, Saint Denis (FR); Michele Mousset, Nogent sur Marne (FR); Marie-Anne Sanchez, Nogent sur Marne (FR); Helene De Clermont Gallerande, Vincennes (FR)

(73) Assignee: Chanel Parfums Beaute, Neuilly sur Seine (FR)

( * ) Notice: Subject to any disclaimer, the term of this patent is extended or adjusted under 35 U.S.C. 154(b) by 305 days.

(21) Appl. No.: 12/666,344

(22) PCT Filed: Jun. 25, 2008

(86) PCT No.: PCT/EP2008/058065
§ 371 (c)(1), (2), (4) Date: Dec. 23, 2009

(87) PCT Pub. No.: WO2009/000849
PCT Pub. Date: Dec. 31, 2008

(65) Prior Publication Data
US 2010/0183535 A1 Jul. 22, 2010

(30) Foreign Application Priority Data

Jun. 25, 2007 (FR) ...................................... 0704534
Mar. 10, 2008 (FR) ...................................... 0851534

(51) Int. Cl.
*A61K 8/00* (2006.01)
*A61Q 1/04* (2006.01)
*A61Q 1/08* (2006.01)
*A61Q 1/10* (2006.01)
*B29C 41/42* (2006.01)

(52) U.S. Cl. ........... 424/488; 424/64; 424/63; 424/70.7; 264/334

(58) Field of Classification Search ........................ None
See application file for complete search history.

(56) References Cited

U.S. PATENT DOCUMENTS

| 3,978,207 | A |   | 8/1976  | Fotiu et al. |
|-----------|---|---|---------|--------------|
| 4,374,796 | A | * | 2/1983  | Ogasawara et al. ........... 264/101 |
| 4,884,601 | A |   | 12/1989 | Hatakeyama et al. |
| 5,063,050 | A |   | 11/1991 | Verdon et al. |
| 5,316,712 | A | * | 5/1994  | Ono et al. ...................... 264/102 |
| 5,401,309 | A | * | 3/1995  | Chopin et al. ................. 106/461 |
| 7,011,821 | B2 | * | 3/2006  | Amato et al. ..................... 424/61 |
| 2004/0175338 | A1 | * | 9/2004 | Filippi et al. ..................... 424/64 |
| 2005/0074474 | A1 | * | 4/2005 | Sako .............................. 424/401 |
| 2006/0147390 | A1 | * | 7/2006 | Schreiber et al. ............... 424/47 |

FOREIGN PATENT DOCUMENTS

| EP | 0628393    | * | 12/1994 |
| FR | 2594409    |   | 8/1987  |
| JP | 362004218  | * | 6/1985  |
| JP | 62190114   |   | 8/1987  |
| KR | 2001073603 | * | 1/2000  |
| WO | 8800039    |   | 1/1988  |
| WO | 03022229   |   | 3/2003  |
| WO | 03080005   |   | 10/2003 |

OTHER PUBLICATIONS

Guler Kimaya (HELIOGEL) (Feb. 2007).*
Rotaru et al. "Silicone rubber mould cast polyethylmethacrylate-hydroxyapatite plate used for repairing a large skull defect" J Craniomaxillofac Surg. Jun. 2006;34(4):242-6. Epub Apr. 27, 2006 (abstract).*
International Search Report dated Aug. 22, 2008 from corresponding PCT/EP2008/058065.

* cited by examiner

*Primary Examiner* — Robert A Wax
*Assistant Examiner* — Danah Al-Awadi
(74) *Attorney, Agent, or Firm* — Young & Thompson

(57) ABSTRACT

A process of manufacturing a solid cosmetic product, includes the steps of applying to a composition based on powder and fluid binder, introduced into a mould, a sheet of porous material having an average pore diameter ranging from 5 to 180 μm; then passing at least some of the volatile solvent through the sheet; removing the volatile solvent that has passed through the sheet and drying the composition in order to solidify it before depositing it in a packaging. The solid product obtained according to this process and to its uses as a face and/or body makeup product are also described.

17 Claims, No Drawings

PROCESS OF MANUFACTURING A SOLID COSMETIC PRODUCT

The present invention relates to a process of manufacturing a solid cosmetic product.

Eye shadows and blushers are made up of an aqueous or anhydrous carrier and dyestuffs intended to give a makeup effect to the skin.

Aqueous-based makeup is conventionally prepared by depositing a paste containing dyestuffs and an aqueous binder onto a small plate, then drying the paste in the oven with a view to removing the water. This process has the drawback of leading to the formation of a "crust" on the surface of the pulverulent product obtained, which needs to be removed. This results not only in a loss of product, but also in a product with an uneven surface.

Application EP-0 628 393 furthermore describes a process of manufacturing a makeup composition in the form of a cake, which consists in pouring a fluid composition into a mould covered with an open-cell plastic and elastic foam (such as a sheet of crosslinked polyurethane), for example through a central opening made in the foam, so as to partially impregnate said foam. The latter makes it possible, while conforming to the dimensional variations of the composition, to simultaneously follow the shrinkage during solidification and to thus obtain a less delicate cake and also to provide a support firmly attached to the cake after solidification.

However, it is obvious that the impregnation in the foam of some of the composition which it will no longer be possible to remove after solidification leads to a loss of product for the consumer.

Moreover, the composition used in EP-0 628 393 generally contains, as binder, an organic solvent or, when it contains plaster, an aqueous solvent. In the latter case, solidification occurs by setting of the plaster, for example over three days. Otherwise it occurs during evaporation of the organic solvent, for example at 40° C. over 55 hours.

These solidification times are incompatible with an industrial process.

Application EP-0 628 393 certainly indicates that the foam may be slightly compressed by a platen during the solidification step. Although this variant may make it possible to accelerate the removal of the water or of the solvent, it is not obvious that it could be used in the case of aqueous-based compositions containing powders other than plaster and/or amounts of water greater than or equal to 50 wt %. This is because, under these conditions, considering the size of the cells of the foam, which is for example around 2000 microns for the foam sold under the name BULPREN S28190, and around 3000 microns for the foam sold under the name BULPREN S30, there is a high risk that, when removing the water, a not insignificant amount of the composition is passed through the foam.

The Applicant has realized that it is desirable to be able to formulate compositions that are rich in water or in volatile solvent in the case where designs imprinted in the wall of the mould must be imparted, with good outline accuracy, to the surface of the cake and/or in the case where it is desired to produce a very smooth and shiny cake.

Furthermore, the thickness of the foam (from 3 to 6 mm) and the need to at least partially impregnate it with the cast composition consequently limit the minimum thickness of the cakes capable of being obtained according to Application EP-0 628 393.

Finally, it is necessary in that application to provide a step of attaching, by bonding or by means of a band, the foam that supports the cake into the packaging in which the cake must be sold, whereas it would, on the contrary, be desirable to optionally be able to obtain at the end of the manufacturing process, a cake capable of being handled as is or attached to a support suitable for being directly snapped on or held by simple introduction into its packaging.

Document FR-2 594 409 furthermore discloses a process of manufacturing cosmetic makeup comprising a step of compressing the composition used in the preparation of the makeup, by means of a compression device comprising a support block for the mould containing this composition and a presser member. Specifically, the composition is compressed between a sliding base plate and the presser member in contact with the upper opening of the mould, a membrane that absorbs the liquids being interposed between the presser member and the surface of the composition. Furthermore, a porous absorbent component, especially made of sintered metal, is provided at the end of the presser member in contact with the membrane and/or on the outer face of the base plate which in this case has an openwork design. The porous absorbent component is intended to absorb the solvent contained in the composition, which is then removed by suction means. The removal of the solvent makes it possible to avoid the formation of cracks and irregularities in the product during drying, which are due to the evaporation of the solvent.

Although the solution proposed in this document makes it possible to remove the water contained in water-rich compositions, it has the drawback of not allowing the manufacture of solid cosmetic products having a surface which is either very smooth, or equipped with designs, considering the need to use a membrane in this process which is continuously applied to the surface in question.

Therefore, there is still a need to have a process of manufacturing solid cosmetic compositions, that are optionally aqueous-based, which can be used under conditions that are economically compatible with an industrial process and which offers an optimum level of product restitution for the consumer. It would also be advantageous to be able to have a process that allows the manufacture of solid cosmetic compositions of any thickness and of any shape, optionally having a very smooth, very shiny or matt surface on which any designs can, if it is desired, be imprinted with high precision.

The Applicant has now demonstrated that these needs can be met by means of a particular process of manufacturing these solid cosmetic compositions, in particular using a sheet of porous material having an average pore size of 5 to 180 μm, onto which a pressure is applied, in order to partially remove the solvent contained in these compositions.

One subject of the present invention is thus a process of manufacturing a solid cosmetic product, comprising the steps consisting in:
1) introducing a composition containing at least one powder and at least one fluid binder comprising a volatile solvent into a mould having a bottom and an opening;
2) applying to said composition a sheet of porous material having an average pore diameter ranging from 5 to 180 μm, which is either in direct contact with said composition, or is separated from the latter by a grid;
3) passing at least some of the volatile solvent through said sheet;
4) removing the volatile solvent that has passed through said sheet to obtain a partially solidified composition;
5) drying said partially solidified composition to obtain a solidified composition;
6) optionally removing said mould and/or said sheet; and
7) placing said solidified composition into a packaging, so as to make the surface previously in contact with the bottom of the mould visible.

As a starting point, it is specified that the term "between" used in the remainder of this description should be understood as also including the limits cited.

The process according to the invention enables the manufacture of a solid cosmetic composition which will be subsequently denoted, for greater simplicity, by "makeup".

The composition used according to the invention contains at least one powder, which may especially be a filler, a pigment, a pearlescent agent or a decorative particle of any shape.

The term "filler" is understood to mean any particle of any shape (especially spherical or lamella), that is mineral or organic, white or colourless, insoluble in the composition and which is generally intended to give body and/or rigidity to the composition and/or to provide softness, mattness and/or uniformity to the makeup. Examples of fillers are talc, mica such as natural or synthetic sericite, calcium or barium sulphate, alumina, aluminium hydroxide, silica and silicates such as hectorites, bentonites, laponites, magnesium aluminium silicates, clays such as kaolin, boron nitride, calcium or magnesium carbonates, hydroxylapatite, glass or ceramic microcapsules, starch, aluminium or calcium salts of starch modified by octenyl succinic anhydride, microcrystalline cellulose, hollow microspheres of vinylidene chloride/acrylonitrile copolymer, polyamides (homopolymers and copolymers) such as Nylon®, poly-β-alanine powders, polyethylene or polypropylene powders, powders of polystyrene and in particular that with the INCI name: Styrene/DBV Copolymer, powders of polyurethane and especially that of INCI name: HDI/Trimethylol Hexylactone Crosspolymer & Silica, polyester powders and in particular polymethyl methacrylate powders, polytetrafluoroethylene (PTFE) powders, silicone resins such as polymethylsilsesquioxane, silicone elastomer powders, lauroyl lysine, silk or pearl powder and synthetic fluorphlogopite, and also soaps (magnesium stearate or myristate). The fillers may especially be made up of several layers having a different chemical nature and/or different physical form and may especially be in the form of lamellae coated with spherical fillers. They may be modified using various surface treatments.

The pigments are white or coloured particles intended to colour or opacify the composition. They may be mineral or organic, natural or synthetic. Examples of mineral pigments are especially oxides of iron, of titanium, of magnesium or of zinc, ferric blue, ultramarines, chromium oxides, manganese oxides, and also composite pigments and goniochromatic, pearlescent, interference, photochromic or thermochromic pigments. Examples of organic pigments are especially carbon black, D&C type pigments, lakes especially based on cochineal carmine, on barium, strontium, calcium and/or aluminium.

The pearlescent agents are iridescent particles that reflect the light. They may be chosen from those conventionally present in makeup products, such as sodium or calcium borosilicates, mica covered with organic and/or mineral pigments such as titanium dioxide or bismuth oxychloride, mica-titanium dioxide covered with organic and/or mineral pigments such as iron oxides, ferric blue or chromium oxide, and also pearlescent pigments based on bismuth oxychloride, flakes based on polyethylene terephthalate or on polyurethane and aluminium-based pearlescent agents.

The pigments and the pearlescent agents may optionally be surface-treated by a hydrophobic agent such as silanes, silicones, soaps of fatty acids, $C_{9-15}$ fluoroalcohol phosphates, acrylate/dimethicone copolymers, mixed $C_{9-15}$ fluoroalcohol phosphate/silicone copolymers, lecithins, carnauba wax, polyethylene, chitosan and optionally acylated amino acids such as lauroyl lysine, disodium stearoyl glutamate and aluminium acyl glutamate.

Other powders that can be used according to the invention are metallic powders of aluminium, of bronze or of iron, for example.

It is preferred that the powder does not comprise calcium sulphate and especially plaster.

Moreover, according to one preferred embodiment of the invention, the powders contain at least one 35-50 μm porous powder, preferably composed of hollow microspheres of ethylene/methacrylate copolymer bonded to silica microspheres via isopropyl titanium triisostearate, such as the powder sold by Kobo under the trade name DSPCS/20N-I2. This type of powder is preferred for a use in matt products. It makes it possible to improve the payoff, the slipperiness and the softness of makeup obtained according to the invention. It also makes it possible to sufficiently aerate the formula to allow good evaporation of the water and thus prevent the makeup from cracking when drying.

The amount of powder contained in the composition used according to the invention preferably ranges from 20 to 80 wt % and more preferably from 30 to 55 wt %, relative to the total weight of the composition.

Besides the aforementioned powder or powders, the composition used according to the invention contains at least one binder comprising a volatile solvent. The expression "volatile solvent" is understood to mean compounds that are liquid at ambient temperature that have a non-zero vapour pressure at ambient temperature and pressure which ranges from $10^{-2}$ to 300 mmHg (1.33 to 40 000 Pa).

Examples of volatile solvents that can be used in the present invention may be chosen from water; hydrocarbon-based oils such as isododecane or isohexadecane; silicone oils such as linear or cyclic polydimethylsiloxanes including octamethylcyclotetra-siloxane, decamethylcyclopentasiloxane, dodecamethyl-cyclohexasiloxane, heptamethylhexyl-trisiloxane, heptamethyloctyltrisiloxane, hexamethyldisiloxane, octamethyl-trisiloxane, decamethyltetrasiloxane, dodecamethylpenta-siloxane; fluorinated oils and mixtures thereof. Mention may also be made of the essential oils forming a perfuming composition. Water is preferred for use in the present invention.

Besides the volatile solvent, the binder may comprise one or more non-volatile water-miscible organic solvents, one or more non-volatile oils and mixtures thereof.

The water-miscible organic solvents may be, for example, chosen from: monoalcohols having from 2 to 6 carbon atoms such as ethanol and isopropanol; and polyols having from 2 to 20 carbon atoms such as glycerol, propylene glycol, dipropylene glycol, butylene glycol, pentylene glycol, hexylene glycol and sorbitol.

In the sense of the present invention, the term "oil" is understood to mean a compound that is liquid at ambient temperature (25° C.) and which, when it is introduced in an amount of at least one 1 wt % into water at 25° C., is not at all soluble in the water, or is soluble up to less than 10 wt %, relative to the weight of oil introduced into the water.

As oils, mention may especially be made of silicone oils, hydrocarbon-based oils, fluorinated oils and mixtures of such oils. The term "silicone oil" is understood to mean an oil comprising at least one silicon atom, and especially at least one Si—O group. The expression "hydrocarbon-based oil" is understood to mean an oil containing only hydrogen and carbon atoms. The expression "fluorinated oil" is understood to mean an oil containing at least one fluorine atom.

Particular examples of oils are constituted by synthetic (poly)esters and (poly)ethers and in particular the (poly)esters of $C_6$-$C_{20}$ acids and/or of $C_6$-$C_{20}$ alcohols that are advantageously branched, such as isononyl isononanoate, isopropyl myristate, 2-ethylhexyl palmitate, hexyl laurate or diisostearyl malate; vegetable oils such as squalane, soybean oil or jojoba oil; branched and/or unsaturated fatty acids such as linoleic or linolenic acid; branched and/or unsaturated fatty alcohols such as octyldodecanol and oleyl alcohol; silicone oils such as linear, optionally phenylated or cyclic polydimethylsiloxanes; fluorosilicone oils; fluorinated oils such as nonafluoromethoxybutane, perfluoromethylcyclopentane, perfluorodimethylcyclohexane, perfluoroperhydrophenanthrene and perfluorodecalin; and also mixtures thereof.

According to one embodiment of the invention, one or more of the oils may be provided by an oily dispersion containing a gelling polymer, at least one surfactant and optionally water. Examples of gelling polymers, capable of gelling oils, are in particular the homopolymers and copolymers of (meth)acrylic acid or of its salts or esters, and also the homopolymers and copolymers of (meth)acrylamide or acrylamido methylpropanesulphonic acid (AMPS). Examples of surfactants are water-in-oil emulsifiers such as oxyethylenated sorbitan esters, fatty alcohol ethers, ethoxylated castor oils, fatty acid polyglycerol esters, phospholipids and silicone-based emulsifiers, especially oxyethylenated and/or oxypropylenated polydimethylsiloxanes, depending on the oils contained in the dispersion, which may, for example, be hydrocarbon-based, vegetable or silicone oils.

The composition used in the first step of the process according to the invention therefore preferably comprises an oily dispersion as described previously, such as the product DC-RM 2051® sold by Dow Corning or the products sold by SEPPIC in the SIMULGEL® and SEPIGEL® ranges.

In particular, it is preferred that such a dispersion is composed of a dispersion of an acrylic copolymer in a mixture of hydrogenated polyisobutene and sunflower seed oil containing polyglyceryl stearate and sunflower phospholipids, such as the product HELIOGEL® sold by LM Cosmetics.

This is because it has been demonstrated by the Applicant that the inclusion of these dispersions, even in a small amount, in the composition used in the process according to the invention make it possible to improve the cohesion of the solid product obtained according to this process, without however observing any unacceptable whitening of the product nor harsh effect after application to the skin. These dispersions are generally used in an amount of 0.05 to 0.5 wt % and preferably in an amount of 0.1 to 0.3 wt %, relative to the total weight of the composition used.

The mixture of powders and of binders leads to the formation of a composition that is in the form of a paste. This composition advantageously contains from 40 to 70 wt % of fluid binder. Moreover, the binder preferably contains from 80 wt % to 100 wt % of volatile solvent and more preferably from 90 wt % to 100 wt % of volatile solvent. This is because it has been observed that the use, in the process according to the invention, of a composition containing this amount of volatile solvent, and in particular of water, could make it possible to obtain a makeup having a very glossy appearance, the surface of which could be coated with a design having very accurate contours.

The composition used in the first step of the process according to the invention may, in addition, contain at least one adjuvant chosen from: surfactants, waxes, gelling agents such as bentonite, latices, fragrances, cosmetic active agents such as antioxidants and phospholipids, polyols (propylene glycol, pentylene glycol, glycerol, mannitol, sorbitol), preservatives (especially parabens and phenoxyethanol) and mixtures thereof.

The surfactants are preferably chosen from oil-in-water emulsifiers. They may especially be at least one compound chosen from optionally polyethoxylated sorbitan esters (such as polysorbate-20), fatty acid glycerol esters, fatty acid sucrose esters or polyesters, fatty acid polyethylene glycol esters, polyether-modified polysiloxanes, fatty alcohol polyethylene glycol ethers, alkyl polyglycosides and hydrogenated lecithin, without this list being limiting.

In the first step of the process according to the invention, the composition described previously is introduced into a mould, which may be constituted of any material preferably resistant to a temperature of 100° C. or even of 150° C., such as a metal, glass, a ceramic material, a polymer resin such as polytetrafluoro-ethylene, polyethylene, polypropylene, polyurethane or a silicone-based material. Silicone moulds are preferred for use in the present invention in so far as they readily withstand the high drying temperatures optionally used in the process and make it possible to give the makeup the precise desired form, on the one hand because it is easier to shape the mould and on the other hand because it enables greater ease of demoulding due to its suppleness and the low adhesion of the paste to the mould. It is thus possible, in particular, to provide a mould that has an undercut shape. Moreover, the bottom of the mould may be flat or concave, depending on whether it is desired to obtain a solid product having a flat or domed visible surface.

The introduction of the composition into the mould may be carried out by any means; it may especially be poured or injected into this mould. For an industrial use of the process according to the invention, it is of course preferred that at least some of the steps of the process are carried out in an automated device. For this purpose, it is preferred that the mould is attached to a locking system that makes it possible to hold the mould in place in the manufacturing device and to introduce an amount of composition in slight excess relative to the volume of the mould, without the composition flowing outside of the device. The introduction of a slightly excessive amount of composition makes it possible to anticipate the shrinkage phenomenon which occurs during subsequent pressing and drying steps.

It is also desirable to be able to introduce a volume of composition that is in excess relative to the volume of the mould when the composition is very fluid and therefore contains a large amount of volatile solvent to be evaporated next, which is generally the case when it is desired to obtain a makeup having a very smooth surface. It may be useful in this case to provide a collar around the mould to prevent the composition from overflowing.

Once the composition has been introduced into the mould, the second step of the process according to the invention consists in applying a sheet of porous material to this composition.

This sheet may be applied either directly to the composition, or separated from it by a grid.

The term "sheet" is understood to mean a porous material of any chemical structure, of any thickness and of any shape adapted to the shape and to the dimensions of the mould. Thus, in the case of a mould with a circular cross section, it is preferred that the sheet takes on the shape of a disc having a diameter slightly smaller than that of the mould. Generally, the thickness of the sheet may be between 0.5 and 10 mm and preferably between 0.5 and 3 mm. This sheet may be disposable.

For this purpose, it is possible to use a sheet comprising at least one material chosen from: polyethylene, polypropylene, polytetrafluoroethylene, polyurethane, a metal or an alloy, glass and non-woven fibres of natural origin such as wool, cotton or felt fibres, or of synthetic origin such as Nylon®. Preferably, the sheet is made up of polyethylene or of polypropylene. It may especially be treated to be hydrophilic or hydrophobic. Sheets of this type are, in particular, commercially available from K2 Technologie under the trade name K2 PLAST®, or from Porex. As a variant, the porous sheet may be made up of fibres and may be in the form of a felt.

Although this embodiment is not ruled out, it is preferred that the sheet is not an open-cell elastic foam.

This is because it is preferred, according to the invention, that the sheet has sufficient rigidity so that it is possible to apply a pressure directly to it without deformation, and for example a rigidity such that the SUR half-cone ref. 180140 (diameter 32 mm; height 16 mm; length 32 mm) of a P734 Normalab Analis penetrometer equipped with a guide rod ref. 180042 (length 162 mm; weight 47.5 g) sinks less than 1 mm, preferably less than 0.5 mm, and more preferably less than 0.1 mm, in the absence of filler, into a 5 mm thick sheet.

As a variant, it is however possible to use more flexible porous sheets, for example made of filter paper or a stainless steel gauze, made of woven fabric or made of Nylon®, in which case it will be advantageous to provide a grid interposed between the porous sheet and the pressure application system optionally used in the rest of the process.

The average diameter of the pores of the sheet of porous material is between 5 and 180 μm, preferably between 10 and 90 μm and more preferably between 20 and 55 μm. The sheet thus makes it possible to readily retain the powder in the mould and thus to guarantee the production of a cosmetic product having, reproducibly, the desired qualitative and quantitative composition which is not possible with a porous material having pores of larger dimensions.

The sheet may advantageously be provided with surface irregularities, suitable for attaching the composition, once it is solidified, to the sheet. These irregularities may especially take the form of concentric projections or grooves or any other shape that makes it possible to achieve the aforementioned objective.

As a variant, the sheet may be combined with a material equipped with surface irregularities suitable for attaching said solidified composition to said sheet. For example, the sheet may be composed of a non-woven material and a plastic mesh may be welded or bonded to this sheet. According to another possibility, a grid may be placed at a distance from the sheet and may be suitable for being immersed in the composition. This grid may be mounted at the centre of a honeycomb screen, for example, and be composed of a crown equipped with radial blades and/or pins. It may, as a variant, take the shape of semicircles. The sheet may then be snapped onto the grid, for example. Furthermore, the screen may itself be provided with a core optionally bearing reliefs such as letters or designs and intended to be covered, on both of its faces, by the composition so as to impart an image to the peripheral surface of the cosmetic product obtained according to the process without however the core being visible through the product.

These embodiments, in which a grid is combined with the sheet, make it possible to impart to the cosmetic product which will be obtained a sufficient solidity with a view to facilitating its handling and its packaging. Moreover, in these embodiments, it is possible to obtain, at the end of the process, a solid product comprising a solidified composition directly or indirectly attached to the sheet and suitable for thus being directly introduced into a packaging with a view to marketing it, the sheet being designed in order to be inserted into the packaging so as to be held in place therein, for example, using a snap-fastening system or by simple adjustment of its dimensions to those of the packaging.

It should be noted that in this step of the process according to the invention, the sheet is not necessarily positioned on the composition, either directly or via the aforementioned grid, as an individualized entity. It may, as a variant, be attached to the end of the presser member used in the third step described below.

In the third step of the process according to the invention, the volatile solvent contained in the composition is passed through the aforementioned sheet, for example after having left the composition to decant naturally or after having centrifuged it (in which case the pulverulent materials fall to the bottom of the mould and the supernatant comprises or is composed of the fluid binder) or preferably by applying a pressure to the sheet by any means and especially by means of a piston. In the latter case, the pressure applied is advantageously between 5 and 400 kg and more preferably between 10 and 250 kg, or even between 150 and 250 kg, for a sheet diameter ranging from 10 to 350 mm. A person skilled in the art will know how to adjust the pressure as a function of the dimensions of the sheet used and of the desired cosmetic quality.

It is in this case advantageous to provide, in the device for manufacturing the solid cosmetic product, an anvil or counter-form system applied against the bottom of the mould and intended to prevent it deforming under the effect of the pressure applied.

At the end of this third step a partially solid composition is thus obtained.

The fourth step of the process according to the invention consists in removing the volatile solvent expelled from the composition. This step may be carried out by suction under vacuum, by gravity (in the case of turning over) or by application of an absorbent material that forms a blotter on the surface of the sheet opposite said composition. According to the invention, a method of suction under vacuum is preferred.

The solidification is carried out in the fifth step of the process according to the invention by drying, especially in air, with infrared rays, with microwaves, at low pressure or in an oven. The purpose of this drying step is to remove the volatile solvent, such as water, optionally remaining in the composition. In order to do this, it is preferred that the composition is dried in an oven set at a temperature of 35 to 150° C. and preferably from 80 to 120° C. Normally, complete drying of the composition may be achieved in thirty minutes to three hours under these conditions.

After drying, the mould may be removed and optionally the sheet as well in order to obtain a solid product of "makeup" type suitable for being inserted into a packaging so as to make the surface previously in contact with the bottom of the mould visible.

In the case where the bottom of the mould is equipped with an undercut intended, for example, to impart a relief to the visible surface of the cosmetic product which is obtained, it may be useful to apply a vacuum to the bottom of the mould in order to facilitate demoulding of the product.

Another subject of the present invention is a solid cosmetic product capable of being obtained by the above process. Depending on whether or not the last step of the process comprises the removal of the porous sheet, this product is in the form of a solid block that may or may not be positioned on said sheet.

It is understood from the preceding that depending on the shape of the mould and the designs optionally imprinted on the bottom of this mould, it is possible, according to the invention, to obtain a solid cosmetic product having a visible surface that takes on any shape, especially in the shape of a dome or a square shape, and equipped with any type of pattern, logo or design, imprinted as an indentation or in relief. The surface of the product could be more or less smooth or shiny, or even have a speckled appearance depending on the constituents and the amount of fluid binder used in the composition employed or depending on the surface appearance, the nature and/or the treatment of the mould. As a variant, it is possible to manufacture, following the process according to the invention, makeup composed of layers of various colours or shades, mixed randomly or separately, or of different powders or textures, corresponding to various compositions superposed in the mould before removal of some of the fluid binder, the dyestuffs used in these compositions being, in this case, advantageously not water-soluble.

The withdrawal from the packaging and application to the skin of the solid product obtained may be carried out by any means and especially using a brush, a powder puff, a sponge or a finger.

The solid product obtained according to the invention may especially be in pulverulent form or in cast pressed cream form and may, in particular, be used as eye shadow, blusher, mascara, product for making up the lips or body or foundation. It may especially be used to make up and/or perfume all or some of the body and/or the face.

Therefore another subject of the present invention is the use of the cosmetic product such as described previously as an eye shadow, blusher, mascara, lip or body makeup product or foundation.

An example of a cosmetic composition capable of being used in the process according to the invention will now be given purely by way of illustration and non-limitingly.

EXAMPLE

Solid Cosmetic Compositions

Compositions containing the following ingredients identified (in capitals) by their INCI names or (in small letters) by their function, the amounts of which are mentioned as weight percentages, were prepared in a conventional manner for a person skilled in the art.

Composition A (Eye Shadow)

| Pulverulent phase: | |
| --- | --- |
| MICA & BISMUTH OXYCHLORIDE | 7.60% |
| Magnesium stearate | 1.20% |
| MICA | 17.56% |
| Preservatives | 0.32% |
| CARMINE | 0.32% |
| Pigments (iron oxides) | 9.40% |
| MANGANESE VIOLET | 3.60% |
| Binder phase: | |
| WATER | 56.07% |
| DIMETHICONE | 0.30% |
| MAGNESIUM ALUMINIUM SILICATE | 0.90% |
| BUTYLENE GLYCOL | 0.60% |
| POLYSORBATE 20 | 0.90% |
| SORBITOL & WATER | 1.20% |
| Preservative | 0.03% |

Composition B (Foundation)

| Pulverulent phase: | |
| --- | --- |
| BORON NITRIDE | 30.00% |
| SILICA & ETHYLENE/METHACRYLATE COPOLYMER & ISOPROPYL TITANIUM TRIISOSTEARATE | 3.00% |
| POLYETHYLENE | 3.00% |
| AMMONIUM SILVER ZINC ALUMINIUM SILICATE | 1.00% |
| Iron oxides | 22.00% |
| TALC | 31.50% |
| MICA | 8.00% |
| Preservatives | 0.50% |
| Fragrance | 1.00% |

5 g of the pulverulent phase were mixed with 7 g of a binder phase such as that given in the preceding example.

Pasty compositions that could be used for manufacturing makeup were obtained.

Composition C (Blusher)

| Pulverulent phase: | |
| --- | --- |
| BORON NITRIDE | 30.00% |
| SILICA & ETHYLENE/METHACRYLATE COPOLYMER & ISOPROPYL TITANIUM TRIISOSTEARATE | 3.00% |
| POLYETHYLENE | 3.00% |
| AMMONIUM SILVER ZINC ALUMINIUM SILICATE | 1.00% |
| Iron oxides | 2.00% |
| RED 7 | 3.00% |
| TALC | 42.50% |
| Pearlescent agents | 14.00% |
| Preservatives | 0.50% |
| Fragrance | 1.00% |

5 g of this pulverulent phase were mixed with 7 g of the following binder phase:

| WATER | 91.30% |
| --- | --- |
| BUTYLENE GLYCOL | 1.00% |
| PENTYLENE GLYCOL | 5.00% |
| SORBITOL & WATER | 2.00% |
| SODIUM ACRYLATES & HYDROGENATED POLYISOBUTENE & PHOSPHOLIPIDS & POLYGLYCERYL-10 STEARATE & HELIANTHUS ANNUUS SEED OIL | 0.20% |
| Preservative | 0.50% |

The invention claimed is:
1. Process of manufacturing a solid cosmetic product, comprising the steps:
 1) introducing a composition containing at least one powder and at least one fluid binder comprising a volatile solvent into a mould having a bottom and an opening;
 2) applying to said composition a sheet of porous material having an average pore diameter ranging from 5 to 180 µm, which is either in direct contact with said composition, or is separated from the latter by a grid;
 3) passing at least some of the volatile solvent through said sheet;
 4) removing the volatile solvent that has passed through said sheet to obtain a partially solidified composition;
 5) drying said partially solidified composition to obtain a solidified composition;
 6) optionally removing said mould and/or said sheet; and

7) placing said solidified composition into a packaging, so as to make the surface previously in contact with the bottom of the mould visible.

2. Process according to claim 1, wherein said powder is chosen from: talc, mica, calcium sulphate, barium sulphate, alumina, aluminium hydroxide, silica, silicates, clays, boron nitride, calcium carbonate, magnesium carbonates, hydroxyapatite, glass, ceramic microcapsules, starch, aluminium, calcium salts of starch modified by octenyl succinic anhydride, microcrystalline cellulose, hollow microspheres of vinylidene chloride/acrylonitrile copolymer, homopolyamides, copolamides, poly-β-alanine powders, polyethylene powders, polypropylene powders, polystyrene powders, polyurethane powders, polyester powders, polytetrafluoroethylene (PTFE) powders, silicone resins, silicone elastomer powders, lauroyl lysine, silk powder, pearl powder, synthetic fluorphlogopite, soaps, oxides of iron, of titanium, of magnesium or of zinc, ferric blue, ultramarines, chromium oxides, manganese oxides, composite pigments, goniochromatic, pearlescent, interference, photochromic and thermochromic pigments, carbon black, D&C type pigments, lakes, sodium or calcium borosilicates, mica covered with organic and/or mineral pigments, mica-titanium dioxide covered with organic and/or mineral pigments, pearlescent pigments based on bismuth oxychloride, flakes based on polyethylene terephthalate or on polyurethane and aluminium-based pearlescent agents.

3. Process according to claim 1, wherein said powder does not comprise calcium sulphate.

4. Process according to claim 1, wherein the powder additionally contains at least one 35-50 μm porous powder.

5. Process according to claim 4, wherein the porous powder is composed of hollow microspheres of ethylene/methacrylate copolymer linked to silica microspheres via isopropyl titanium triisostearate.

6. Process according to claim 1, wherein the composition used in the first step contains from 40 to 70 wt % of fluid binder, relative to the total weight of the composition.

7. Process according to claim 1, wherein the fluid binder contains from 80 to 100 wt % of volatile solvent.

8. Process according to claim 7, wherein the fluid binder contains from 90 to 100 wt % of volatile solvent.

9. Process according to claim 1, wherein the sheet of porous material comprises at least one material chosen from: polyethylene, polypropylene, polytetrafluoroethylene, polyurethane, a metal, an alloy, glass fibers and non-woven fibres of natural origin or of synthetic origin.

10. Process according to claim 1, wherein the sheet of porous material is not an open-cell elastic foam.

11. Process according to claim 1, wherein the volatile solvent is removed by applying a pressure to the sheet that ranges from 5 to 400 kg.

12. Process according to claim 11, wherein the volatile solvent is removed by applying a pressure to the sheet that ranges from 10 to 250 kg.

13. Process according to claim 1, wherein the composition used in the first step contains an oily dispersion comprising a gelling polymer, at least one surfactant and optionally water.

14. Process according to claim 13, wherein the composition used in the first step contains a dispersion of an acrylic copolymer in a mixture of hydrogenated polyisobutene and sunflower seed oil containing polyglyceryl stearate and sunflower phospholipids.

15. Process according to claim 1, wherein the sheet is provided with surface irregularities suitable for attaching said solidified composition to said sheet.

16. Process according to claim 1, wherein the sheet is combined with a material provided with surface irregularities suitable for attaching said solidified composition to said sheet.

17. Process according to claim 1, wherein the mould is made of silicone.

* * * * *